United States Patent
Zlochiver (10) Patent No.: US 12,318,222 B2
(45) Date of Patent: *Jun. 3, 2025

(54) METHOD AND APPARATUS FOR ACCURATE PLACEMENT OF ELECTROCARDIOGRAM ELECTRODES

(71) Applicant: Welch Allyn, Inc., Skaneateles Falls, NY (US)

(72) Inventor: Sharone Zlochiver, Mequon, WI (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 561 days.

This patent is subject to a terminal disclaimer.

(21) Appl. No.: 17/492,130

(22) Filed: Oct. 1, 2021

(65) Prior Publication Data
US 2022/0015705 A1 Jan. 20, 2022

Related U.S. Application Data

(63) Continuation of application No. 16/249,968, filed on Jan. 17, 2019, now Pat. No. 11,134,895.

(51) Int. Cl.
*A61B 5/00* (2006.01)
*A61B 90/00* (2016.01)
(Continued)

(52) U.S. Cl.
CPC ............ *A61B 5/6842* (2013.01); *A61B 5/704* (2013.01); *A61B 90/361* (2016.02); *A61B 90/39* (2016.02);
(Continued)

(58) Field of Classification Search
CPC ..... A61B 5/6842; A61B 5/704; A61B 90/361; A61B 90/39; A61B 2090/363;
(Continued)

(56) References Cited

U.S. PATENT DOCUMENTS 6,282,440 B1 8/2001 Brodnick et al.
8,577,439 B2 11/2013 Pinter et al.
(Continued)

FOREIGN PATENT DOCUMENTS

CN 108618776 10/2018
EP 3384832 10/2018
(Continued)

*Primary Examiner* — Mark W. Bockelman
(74) *Attorney, Agent, or Firm* — Lee & Hayes, P.C.

(57) ABSTRACT

A method for guiding electrocardiogram (ECG) electrode placement on a person includes acquiring an image of the person, identifying an externally discernable anatomical landmark on the image, determining target locations for first through nth electrodes as a function of the location of the landmark, and highlighting the target locations on the person. A system for guiding placement of ECG electrodes comprises an imaging device, an illumination source, a processor, and machine readable instructions. The instructions, when executed by the processor, identify at least one marker in an image acquired by the imaging device, determine, as a function of the location of the at least one marker, target locations on the person at which first through nth ECG electrodes should be placed, and cause the illumination source to illuminate the first through nth target locations.

20 Claims, 10 Drawing Sheets (51) Int. Cl.
*G06T 7/33* (2017.01)
*G06T 7/73* (2017.01)
*H04N 13/204* (2018.01)

(52) U.S. Cl.
CPC ............... *G06T 7/337* (2017.01); *G06T 7/74* (2017.01); *H04N 13/204* (2018.05); *A61B 2090/363* (2016.02); *A61B 2090/395* (2016.02); *G06T 2207/10028* (2013.01); *G06T 2207/20221* (2013.01); *G06T 2207/30004* (2013.01); *G06T 2207/30204* (2013.01)

(58) Field of Classification Search
CPC ............ A61B 2090/395; A61B 5/0077; A61B 2090/3937; A61B 90/36; A61B 2090/366; G06T 7/337; G06T 7/74; G06T 2207/10028; G06T 2207/20221; G06T 2207/30004; G06T 2207/30204; G06T 2207/10004; H04N 13/204
See application file for complete search history.

(56) References Cited

U.S. PATENT DOCUMENTS

| | | |
|---|---|---|
| 8,903,477 B2 | 12/2014 | Berkner |
| 9,220,430 B2 | 12/2015 | Albert |
| 9,802,034 B2 | 10/2017 | Elghazzawi et al. |
| 9,883,835 B2 | 2/2018 | Kue |
| 2015/0320331 A1 | 11/2015 | van Dam et al. |
| 2018/0049659 A1 | 2/2018 | Briante et al. |
| 2018/0132741 A1 | 5/2018 | Martinez Climent et al. |

FOREIGN PATENT DOCUMENTS

| | | |
|---|---|---|
| KR | 20160058277 | 5/2016 |
| WO | 2017099582 | 6/2017 |

METHOD AND APPARATUS FOR ACCURATE PLACEMENT OF ELECTROCARDIOGRAM ELECTRODES

CROSS-REFERENCE TO RELATED APPLICATIONS

This application is a continuation of, and claims priority to, U.S. application Ser. No. 16/249,968, filed on Jan. 17, 2019, which is incorporated herein by reference.

The subject matter described herein relates to systems and methods for accurate placement of electrocardiogram (ECG) electrodes on a person.

BACKGROUND

A typical twelve lead electrocardiogram (ECG) apparatus includes ten electrodes which are placed on (removably adhered or attached to) a person's torso in order to detect the electrical activity of the person's heart. The resulting waveforms show the rhythm and electrical activity of the heart and can provide the skilled clinician with valuable information about the person's cardiac health.

Four of the ten electrodes are referred to as limb or peripheral electrodes and are placed on the person's limbs (arms and legs), one electrode per limb. The other six electrodes are referred to as chest or precordial electrodes. The precordial electrodes are usually identified as electrodes V1 through V6, and are intended to be attached to the person's chest at prescribed locations relative to the person's heart. Obtaining optimal and consistently interpretable ECG waveforms requires precise placement of at least the precordial electrodes (the waveforms are less sensitive to mispositioning of the peripheral electrodes).

Correct positioning of the electrodes relative to the person's heart is usually described in terms of positioning relative to the person's ribs and intercostal spaces, which a clinician should be able in principle to locate easily in most persons. Nevertheless, it is estimated that the occurrence rate of incorrect electrode positioning (defined as electrode displacement greater than 1 cm) by trained technicians can be as high as 50%, with displacements reaching as high as 6 cm (Kania et al. "The effect of precordial lead displacement on ECG morphology", Med Biol Eng Comput 52:109-119, 2014). Such incorrect electrode placement could compromise the diagnostic value of the ECG results. For example, incorrect ECG diagnosis due to incorrect electrode placement was found in 17-24% of patients in one study, including significant diagnostic errors like incorrect recognition of infarction, ventricular hypertrophy, or false diagnosis of ischemia (Bond et al. "The effects of electrode misplacement on clinicians' interpretation of the standard 12-lead electrocardiogram", Eur J Intern Med 23:610-615, 2012). In some cases, for example if the person is obese, it may be more difficult to locate the person's ribs and intercostal spaces, thus increasing the likelihood of incorrect electrode placement.

Therefore, there is a need for systems and methods that will assist the clinician in placing ECG electrodes at the correct locations on the person being evaluated.

SUMMARY

A method for guiding electrocardiogram (ECG) electrode placement on a person includes acquiring an image of the person, identifying an externally discernable anatomical landmark on the image, determining target locations for first through nth electrodes as a function of the location of the landmark, and highlighting the target locations on the person.

A system for guiding placement of ECG electrodes comprises an imaging device, an illumination source, a processor, and machine readable instructions. The instructions, when executed by the processor, identify at least one marker in an image acquired by the imaging device. The instructions also determine, as a function of the location of the at least one marker, target locations on the person at which first through nth ECG electrodes should be placed, and cause the illumination source to illuminate the first through nth target locations.

BRIEF DESCRIPTION OF THE DRAWINGS

The foregoing and other features of the various embodiments of the occupant support structure and method described herein will become more apparent from the following detailed description and the accompanying drawings in which.

DETAILED DESCRIPTION

The present invention may comprise one or more of the features recited in the appended claims and/or one or more of the following features or combinations thereof.

In this specification and drawings, features similar to or the same as features already described may be identified by reference characters or numerals which are the same as or similar to those previously used. Similar elements may be identified by a common reference character or numeral, with suffixes being used to refer to specific occurrences of the element. Examples given in this application are prophetic examples.

Figure 1:
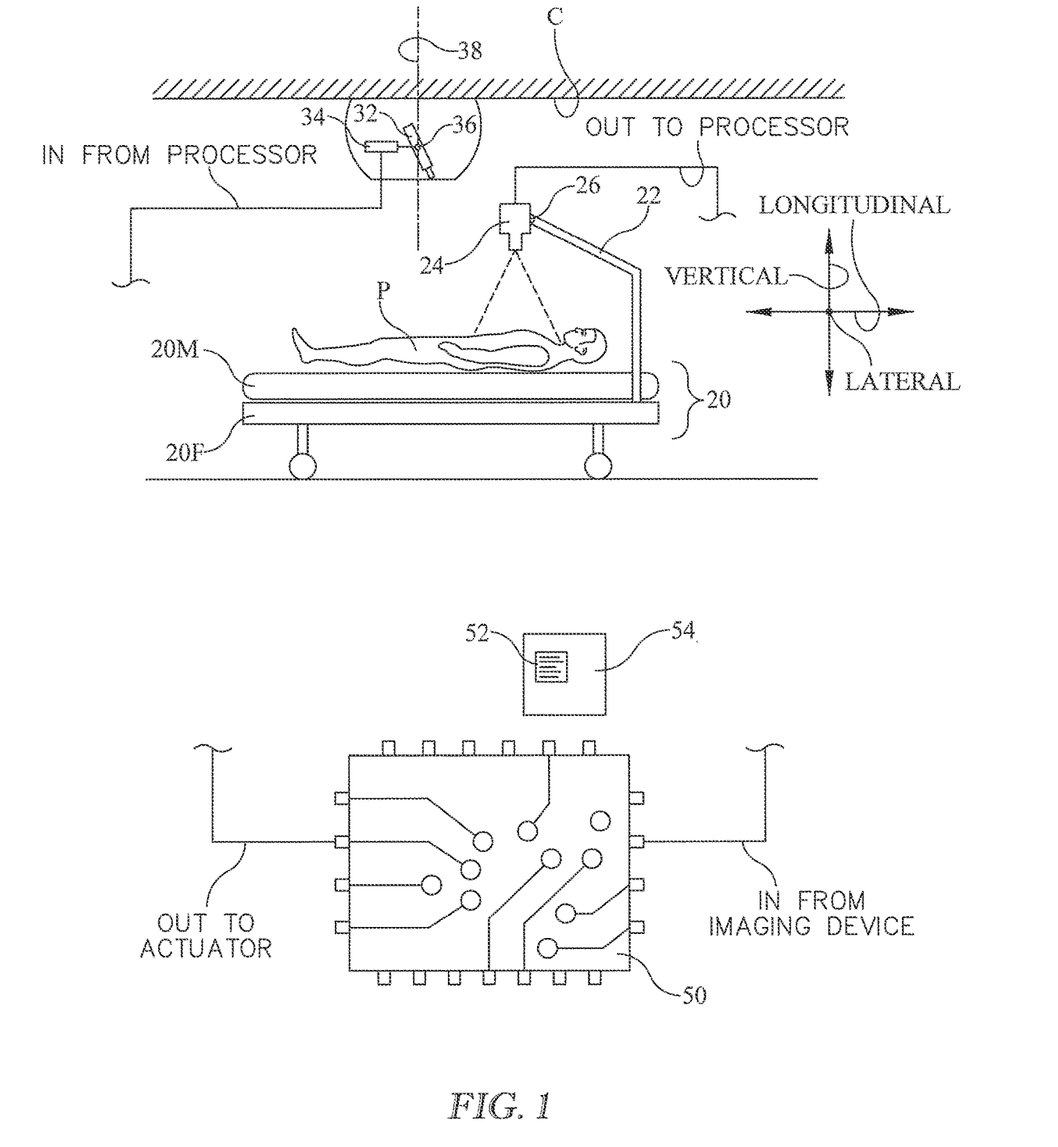
FIG. 1 is a schematic view showing a support platform with a person P supported thereon, an imaging device, a projector rotatable about pitch and yaw axes, a processor, and machine readable instructions which are executable by the processor.

FIG. 1 shows a person P, such as a patient in a medical care facility, lying on and supported by a support platform 20. The illustrated support platform includes a frame 20F and a mattress 20M. The drawing also shows longitudinal, lateral, and vertical reference axes.

A support 22 is affixed to the frame. An imaging device 24 is attached to the support at an attachment 26. Examples of imaging devices include a two dimensional (2D) camera capable of acquiring two dimensional images and a three dimensional (3D) camera capable of acquiring three dimensional images. For convenience, this specification uses the example of a camera which acquires images at wavelengths in the visible portion of the electromagnetic spectrum, with no intent to limit "imaging device" to the specific example of a camera. Moreover, the sensitivity of the imaging device need not be limited to visible portions of the electromagnetic spectrum. The camera is one component of a system for guiding placement of electrocardiogram (ECG) electrodes on the person.

Support 22 and/or attachment 26 may be designed so that the camera is fixed in space and orientation relative to the frame at all times. Alternatively the support and/or attachment may be designed so that the spatial position and/or orientation of the camera is adjustable, but can nevertheless be secured or otherwise maintained in a fixed position and orientation relative to the frame. The person undergoing examination is instructed to remain as motionless as possible. Therefore, when the imaging device is in a fixed position and orientation relative to the frame it is also in a substantially fixed position and orientation relative to the patient.

The system for guiding placement of the ECG electrodes also includes an illumination source, such as visible light projector 32, which is illustrated as mounted on the ceiling C of the facility. In another embodiment the light source is mounted on support platform frame 20F. If desired the light may be polarized or coherent. An actuator 34 is coupled to the projector. In practice, and as described in more detail below, the actuator responds to commands which cause it to rotate the projector about at least a projector pitch axis 36 (perpendicular to the plane of the illustration) and a yaw axis 38. As a result, light emitted from the projector can be aimed at specified target locations on the person's body.

The system for guiding placement of the ECG electrodes also includes a processor 50 and machine readable instructions 52 which are executable by the processor. The instructions are shown as being stored in a memory 54.

Figure 2:
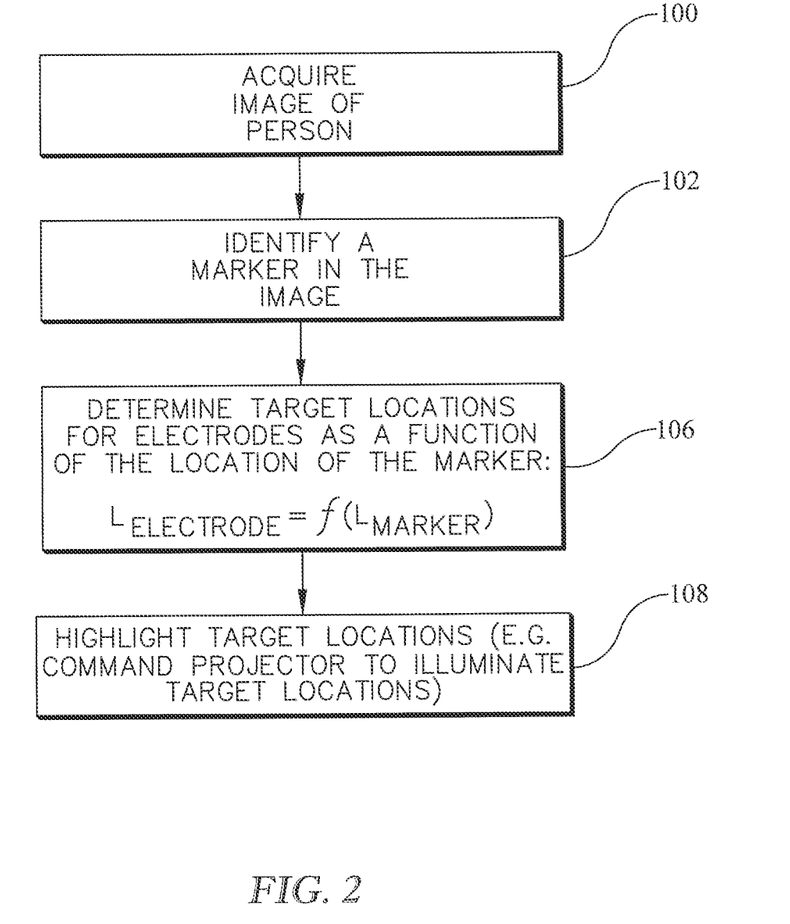
FIG. 2 is block diagram showing method steps for guiding placement of electrocardiogram (ECG) electrodes on the person of FIG. 1 or, equivalently, showing functional attributes of a system for guiding placement of the ECG electrodes.

FIG. 2 is a block diagram related to guiding placement of ECG electrodes on a person P. The blocks of the block diagrams referred to in this specification correspond to tasks which machine readable instructions 52 carry out when those instructions are executed by the processor. Equivalently, the blocks correspond to tasks the processor carries out when operating according to the instructions. According to either point of view the blocks represent method steps and also represent attributes of the system for guiding placement of electrocardiogram (ECG) electrodes.

At block 100 the camera acquires an image of the person P. At block 102 the machine readable instructions 52, when executed by processor 50, identify at least one marker in the image acquired by the camera. In one embodiment the marker is an externally discernable anatomical landmark on the image. Examples of externally discernable landmarks include external features of the body such as the nipple, the areola, or an aspect of an anatomical contour that corresponds to, for example, the lateral edges of the sternum or the sternal angle, or the lateral borders of the rib cage. Other examples of externally discernable landmarks include internal features of the body, such as a rib or intercostal space, which, despite being internal, are nevertheless easy to perceive and identify, at least in some persons. For example the ribs and intercostal spaces of a slender person may be easy to perceive and identify.

At block 106 the method determines target locations on the person at which first through nth ECG electrodes should be placed. The target locations are determined as a function of the location of the one or more markers identified at block 102. For example, the correct location on the body for the V1 electrode is at the fourth intercostal space adjacent to the right edge of the person's sternum. Therefore, identification of the person's right fourth intercostal space and the right edge of the person's sternum at step 102 may be used to determine the correct location for the V1 electrode. A target location may be determined as a function of a single marker or as a function of multiple markers. The marker or markers used to determine one target location may differ from the marker or markers used to determine some other target locations.

In some cases the literature describes the correct location for an electrode in terms of the correct location of other electrodes. For example, the location for V3 is often described as midway between V2 and V4. The correct location for V3 is nevertheless considered to be a function of the location of the one or more markers identified at block 102 because the location(s) of the marker or markers formed the basis for determining the correct locations for V2 and V4. Therefore, although the location of V3 may be an explicit function of the locations of V2 and V4, it is an implicit function of the marker or markers.

At block 108 the method highlights the target locations on the person. In one specific example the machine readable instructions 52, when executed by processor 50, cause projector 32 to illuminate the first through nth target locations with visible light. In other words at block 108 the method issues a command which is a consequence of execution of the machine readable instructions by the processor. The command is issued to actuator 34 and causes the actuator to aim the projector at the target location so that the light emitted by the projector shines on the target location.

Once a target location is illuminated as described above, the clinician may place the corresponding electrode at the illuminated target location with confidence that the electrode placement is correct.

Figure 3:
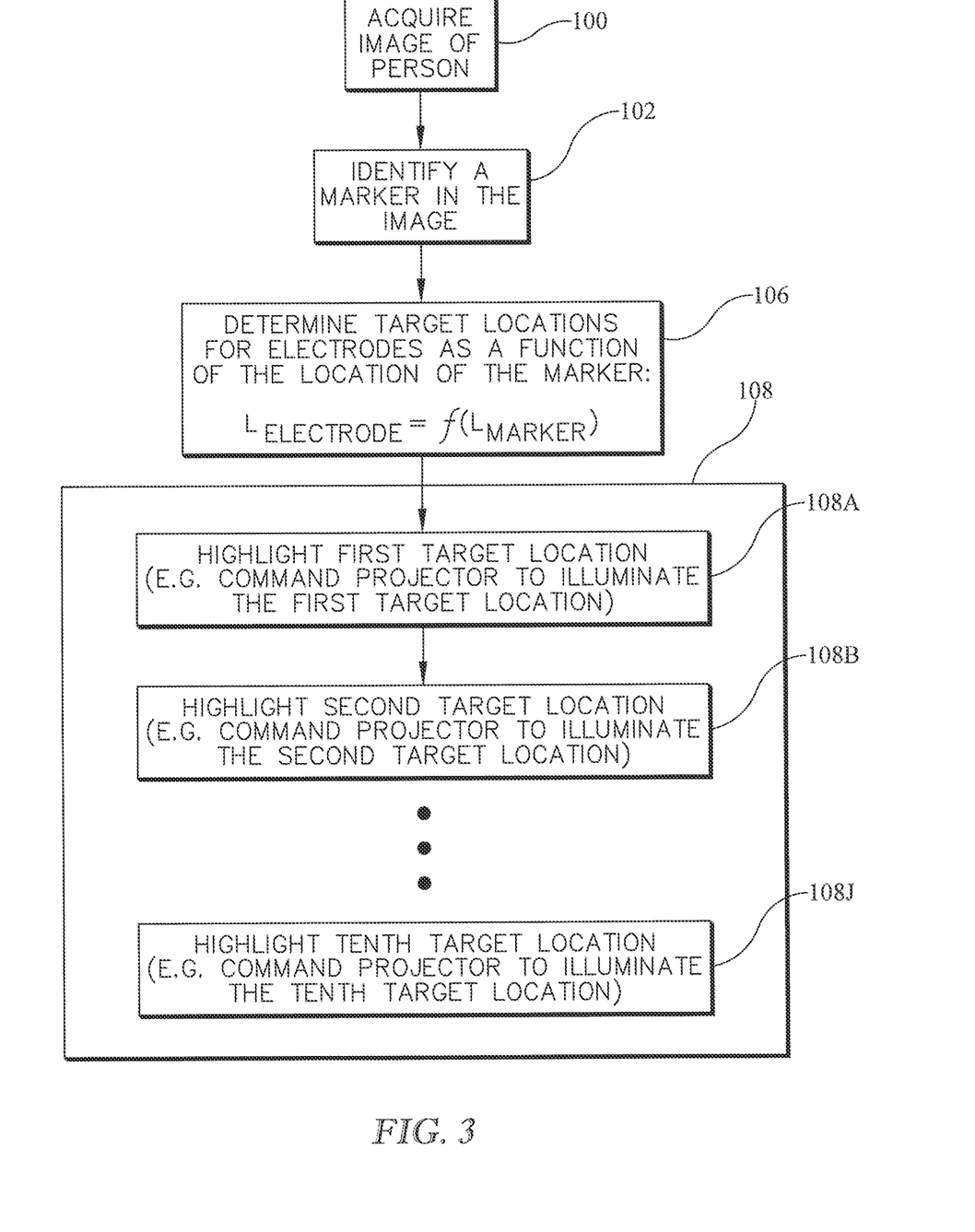
FIG. 3 is a block diagram similar to FIG. 2 showing an embodiment in which correct target locations for the electrodes on the person's body are highlighted one at a time.

The first through nth target locations may be highlighted one at a time, i.e. in a temporal sequence. This is shown at sub-blocks 108A-108J of main block 108 of FIG. 3. The A through J suffixes correspond to the ten electrodes. FIG. 3 also shows that all target locations have been determined at block 106 before any target location is illuminated at block 108. However this is not a requirement in either this or other embodiments. All that is necessary is for the determination of a given target location to be carried out before that target location can be illuminated.

Figure 4:
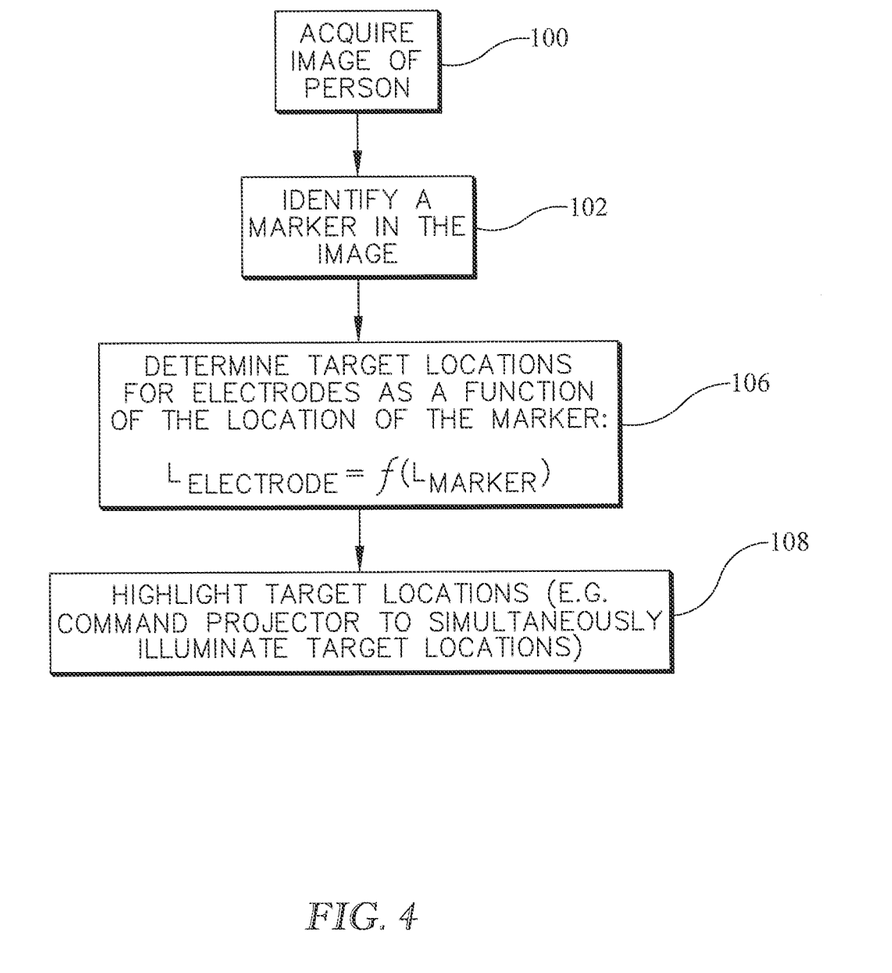
FIG. 4 is a block diagram similar to FIG. 2 showing an embodiment in which the correct target locations for the electrodes on the person's body are all highlighted simultaneously.

In another embodiment, seen in FIG. 4, the first through nth target locations are highlighted simultaneously. FIG. 4 is identical to FIG. 1 except that block 108 expressly specifies simultaneous illumination.

Figure 5:
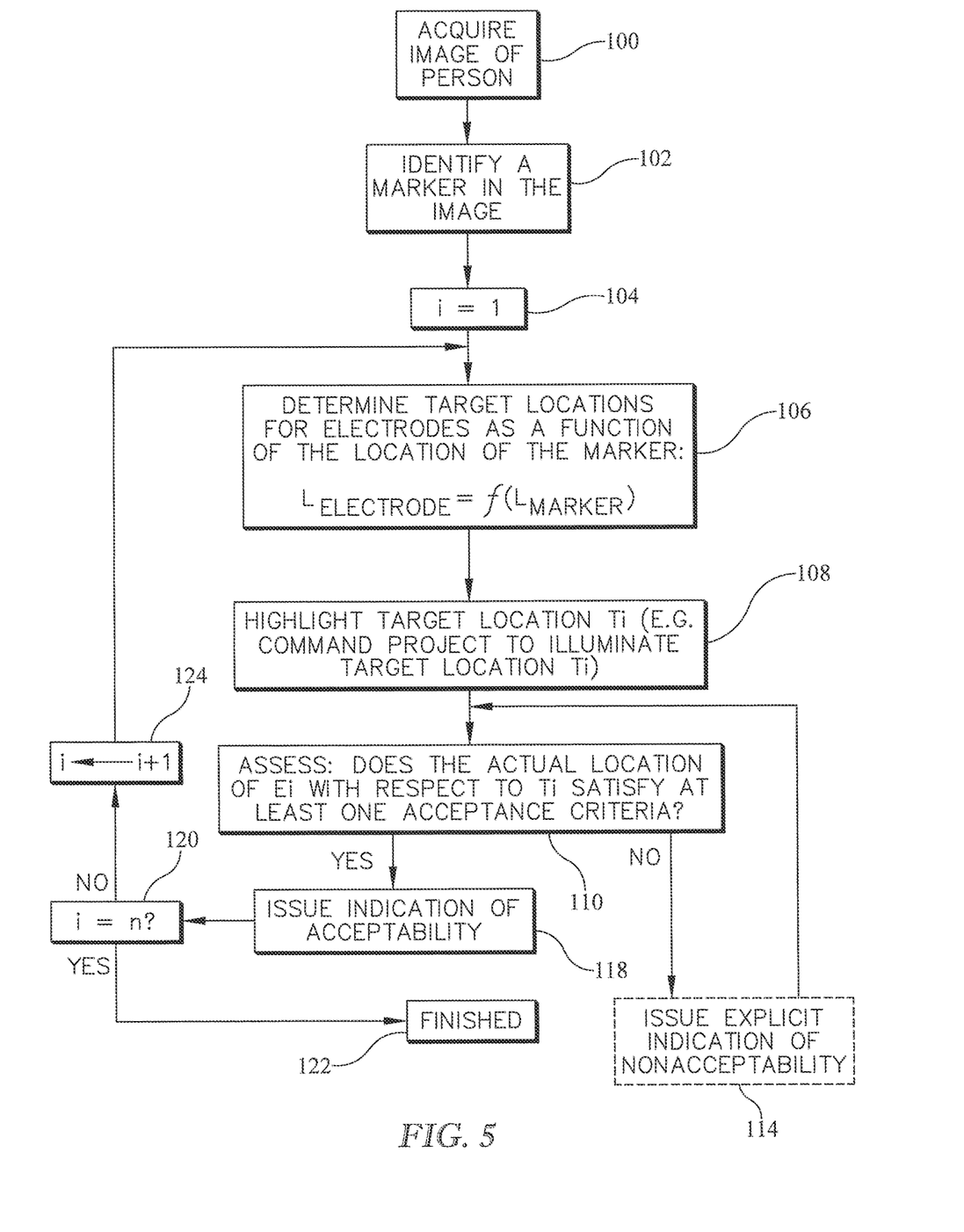
FIG. 5 is a block diagram similar to FIG. 1 including feedback logic for determining if electrodes associated with each target location on the person's body is satisfactorily positioned on the person.

Referring now to FIG. 5, the system may include feedback for determining if an actual electrode $E_i$ (i=1, 2, . . . n)

associated with each target location $T_i=(i=1, 2, \ldots n)$ is satisfactorily positioned on the person. Blocks 100, 102 and 106 are the same as blocks 100, 102 and 106 of FIG. 1 except that index initialization block 104 resides between blocks 102 and 106. At block 108 the system highlights the ith target location $T_i$, corresponding to index i=1.

Figure 6:
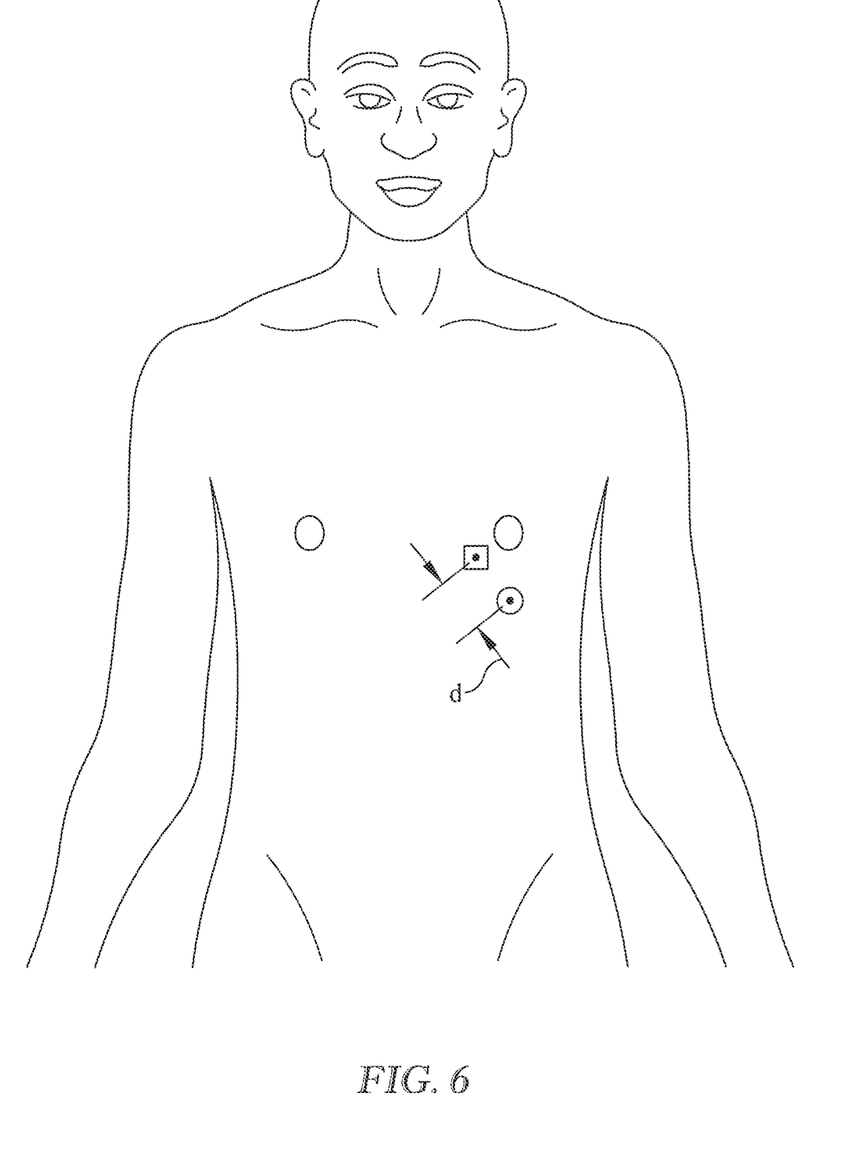
FIG. 6 is a view of a person showing a target location for an ECG electrode and an actual location of the electrode.

At block 110 the method assesses whether or not the actual location of an electrode $E_i$ and the target location $T_i$ for that electrode satisfy an acceptance criterion or criteria. For example, referring additionally to FIG. 6, the system may determine the offset distance d between the center of the target location $T_i$ and the center of the electrode $E_i$ and compare the distance d to an acceptance criterion such as a maximum acceptable offset $d_{MAX}$ between the target and the electrode.

In response to the assessment at block 110, the system and method issue an electrode placement status indication, i.e. an indication of whether the actual location of the electrode satisfies the acceptance criterion, and therefore is acceptable, or violates the acceptance criterion and therefore is unacceptable. A status indication of non-acceptability need not be overt. Instead it may take the form of the absence of an indication of acceptability.

Continuing to refer to FIG. 5, if the assessment at block 110 is that the electrode has not been placed at the correct location, the method and system follow the "NO" path and continue to carry out the assessment of block 110. Block 114 shows the option that an express or overt indication of non-acceptability may be generated and conveyed to the clinician. The optional nature of the overt indication of unacceptability is signified by the dashed border of block 114. One example of an express indication of non-acceptability is illumination of a warning light on the ECG apparatus.

If the assessment at block 110 is that the electrode has been placed at the correct location, the method and system follow the "YES" path to block 118. At block 118 the system issues a status indication of "acceptable" with respect to the electrode under consideration. At block 120 the method tests whether placement of the electrodes is complete, i.e. whether all n electrodes have been correctly positioned on the person's body. If so, the system branches to FINISHED at block 122 and may also provide an indication that all the electrodes have been correctly placed on the person. If not, the method advances to block 124, increments index i, and returns to block 106.

Figure 7:
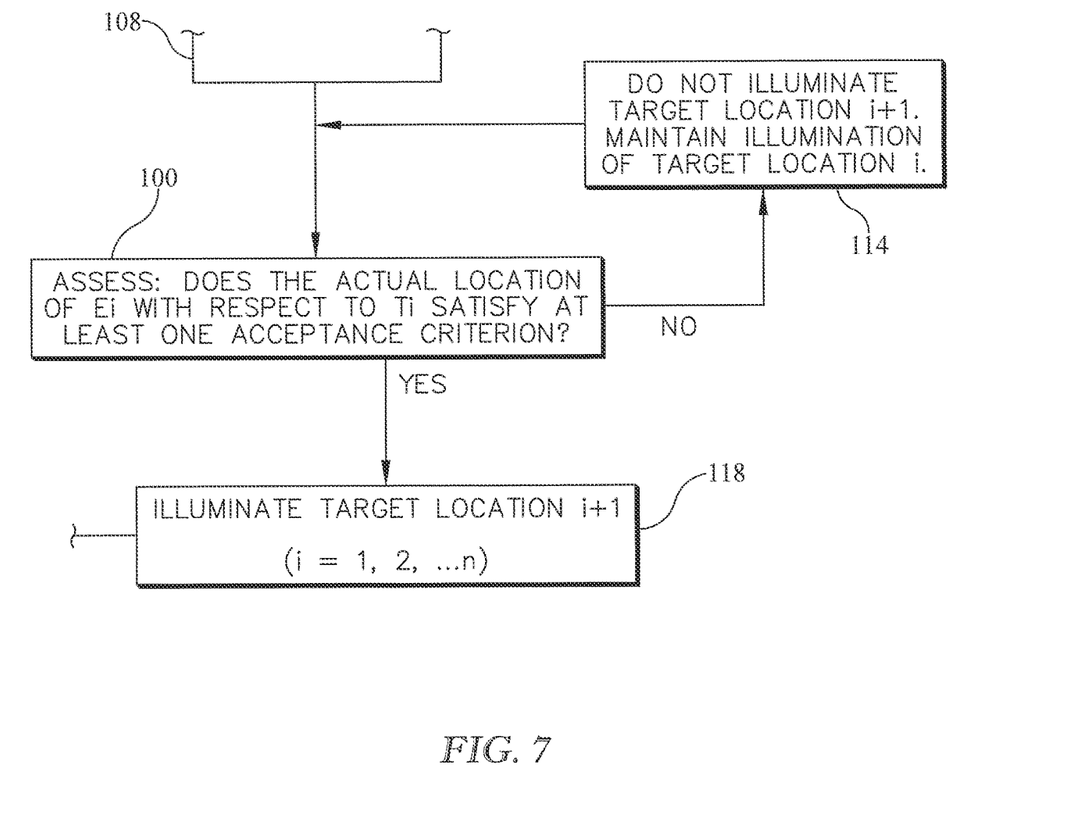
FIG. 7 is a fragment of the block diagram of FIG. 5 showing one specific embodiment of indicating the status (acceptable or unacceptable) of the location of a particular ECG electrode.

FIG. 7 is a fragment of the block diagram of FIG. 5 showing one specific embodiment of indicating the status (acceptable or unacceptable) of the location of a particular electrode currently under consideration. If the assessment at block 110 is that the ith electrode has not been correctly positioned at the ith target location, the method follows the "NO" path to block 114 where it maintains the illumination of target location i, and refrains from illuminating the next target location in sequence, i.e. target location i+1. Conversely, if the assessment at block 110 is that the ith electrode has been correctly positioned at the ith target location, the method follows the "YES" path 116 to block 118 where it illuminates the next target location in sequence, i.e. target location i+1. Stated formally, the non-acceptable status of electrode placement at target location $T_i$ (i=1, 2, \ldots n-1) is indicated by refraining from highlighting a next target location $T_{i+1}$ (i=2, 3, \ldots n) until the assessment at block 110 reveals that the placement of electrode $E_i$ satisfies at least one acceptance criterion with respect to the currently highlighted target location $T_i$. Stated less formally, the system maintains illumination of the current target location until the acceptance criterion for correct placement of the electrode at that location has been satisfied. The system proceeds to illuminate the next target location only after the acceptance criterion for the current target location has been satisfied.

Figure 8:
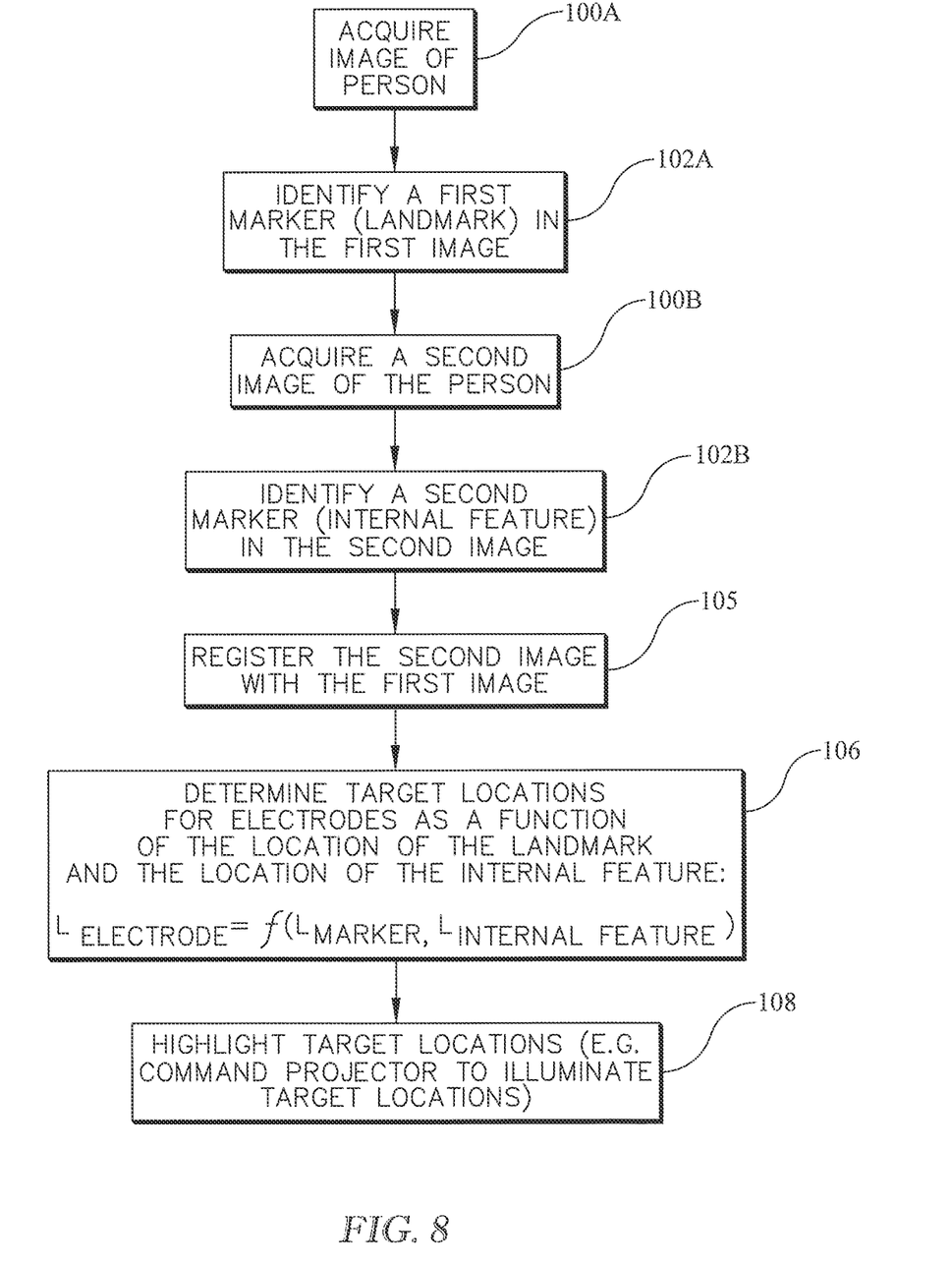
FIG. 8 is a block diagram showing an embodiment in which two images are acquired and registered with each other in connection with guiding placement of the ECG electrodes.

Although a clinician can usually locate externally discernable anatomical landmarks which are useful for correct placement of ECG electrodes, those landmarks may be more difficult to find on some people. FIG. 8 shows an embodiment which addresses that difficulty by acquiring two images. At block 100A the method acquires a first image which includes a first marker, specifically an externally discernable marker (a landmark) as already described. Block 102A identifies the first marker. At block 100B the method acquires a second image of the person which includes a second marker, i.e. one or more internal structures which are discernable features in and of themselves, or which include or define internal features. Examples of the second image include x-ray and magnetic resonance (MRI) images. Block 102B identifies at least one of the discernable internal features. Examples of discernable internal features include skeletal related features such as the clavicles, ribs, intercostal spaces, sternum, and the relationships among them (e.g. the line of union between the body of the sternum and the manubrium, which is often referred to as the sternal angle).

Figure 9:
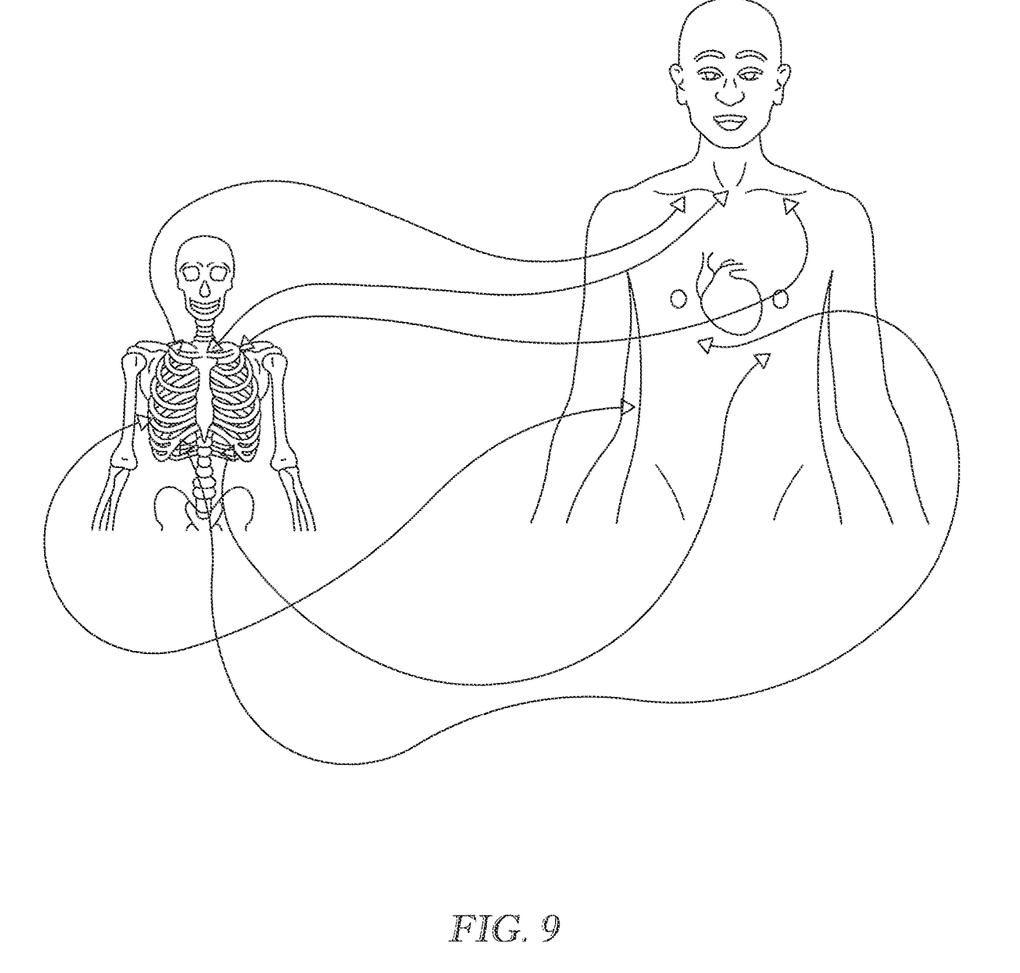
FIG. 9 is a non-numerical example of how a registration technique can correlate features of a person's internal anatomical structures with externally discernable landmarks on the person's body.

At block 105 the system employs a registration technique or algorithm to register the second image with the first image. Registration exposes the relationship(s) between the second marker or markers (discernable internal feature(s)) and the first marker or markers (externally discernable feature(s)). Registration techniques which may be useful are described in "A Survey of Image Registration Techniques" by Lisa Gottesfeld Brown, Department of Computer Science, Columbia University, New York, N.Y. 10027, dated Jan. 12, 1992. FIG. 9 is an example of how the person's clavicles, lowermost ribs, rib cage lateral boundaries and sternal angle may be spatially correlated to externally discernable landmarks such as body contours so that the two images can be registered.

Returning to FIG. 8, at block 106 the system determines the target locations as a function of the location of the at least one identified landmark (first marker) and the location of the at least one internal feature (second marker).

At block 108 the system commands illumination of the target locations. The clinician places the electrodes at those highlighted locations. Although the clinician is guided by the highlighting of external locations on the person's body, the registration of the first and second images causes those highlighted external locations to correspond to the internal features of actual interest.

The block diagram of FIG. 8 may be thought of as a two image version of the single image embodiment of FIG. 1. Accordingly, the variants and adaptations of FIGS. 3, 4, 5 and 7 (sequential illumination, simultaneous illumination, and feedback) may be applied to the embodiment of FIG. 8.

Figure 10:
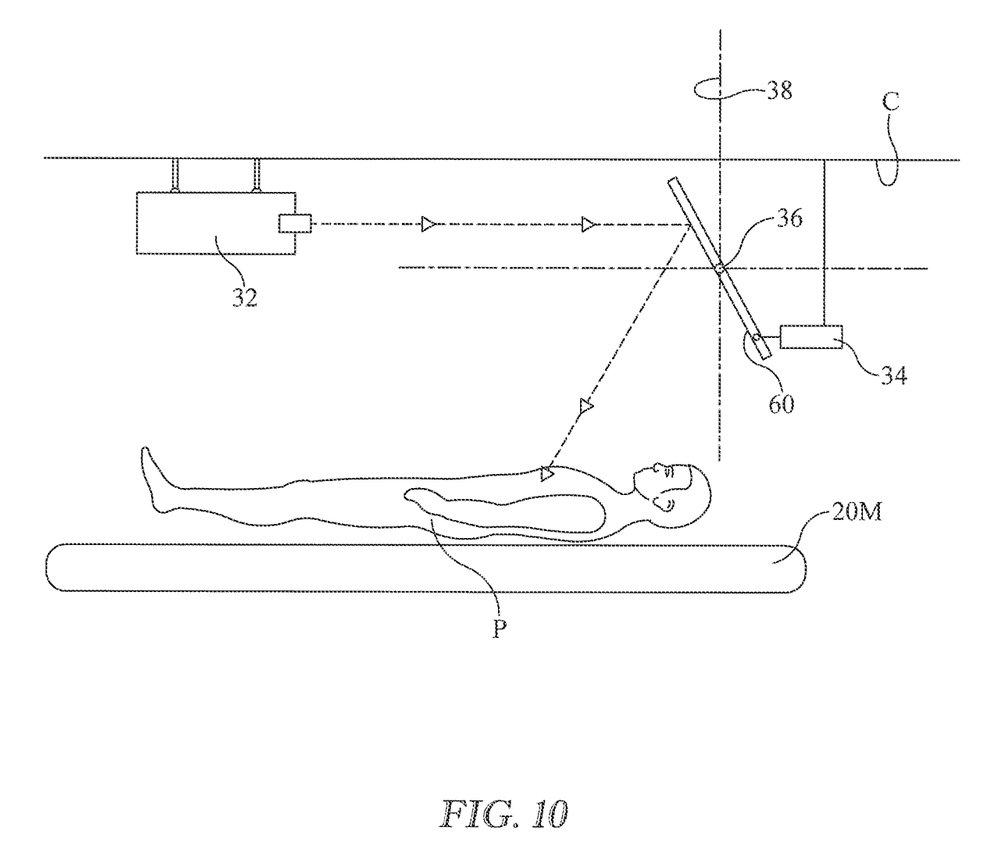
FIG. 10 is a view similar to FIG. 1 in which a mirror rather than the projector is rotatable about pitch and yaw axes.

FIG. 10 shows an alternative to the arrangement of FIG. 1 for directing the light emissions of projector 32 to the target locations. The alternative arrangement includes a projector 32 which, unlike the projector of FIG. 1, is not rotatable about pitch and yaw axes. Instead, the illustrated projector is immovably mounted to the ceiling. One or more optical elements, illustrated as a mirror 60, is pivotably mounted so that it can be rotated about pitch and yaw axes 36, 38. An actuator 34 is coupled to the mirror. The actuator responds to commands (from block 108 of the various block diagrams) which cause it to rotate the mirror about the pitch and/or yaw axes in order to direct the light (dashed line with arrowheads) to the target location on the person's body.

Although this disclosure refers to specific embodiments, it will be understood by those skilled in the art that various changes in form and detail may be made without departing from the subject matter set forth in the accompanying claims.

The invention claimed is:

1. A method for guiding electrocardiogram (ECG) electrode placement on a person, comprising:
    identifying, with a processor, at least one externally discernable anatomical landmark illustrated in an image of the person;
    acquiring, with the processor, an additional image illustrating an internal anatomical structure of the person;
    identifying, with the processor, at least one internal feature of the person based on the additional image;
    determining, with the processor, and based on a first location of the at least one landmark, and a second location of the at least one internal feature, target locations on the person at which first through nth ECG electrodes should be placed; and
    causing, with the processor, an illumination source to highlight the target locations on the person with visible light.

2. The method of claim 1 wherein the first through nth target locations are highlighted one at a time.

3. The method of claim 2 wherein an electrode is associated with each target location, and the method includes:
    assessing, with the processor, whether an actual location of each electrode with respect to its target location satisfies at least one acceptance criterion, and, in response to the assessing step, and
    issuing, with the processor, an electrode placement status indication.

4. The method of claim 3 wherein the status indication is a non-acceptability indication, the method further comprising refraining from highlighting a next target location $T_{i+1}$ (I=2, 3, . . . n) until the assessment reveals that the currently highlighted target location $T_i$ (I=1, 2, . . . n−1) satisfies the at least one acceptance criterion.

5. The method of claim 1 wherein the first through nth target locations are highlighted simultaneously.

6. The method of claim 1 wherein the illumination source is coupled to an actuator, the actuator being adapted to move the illumination source, in response to a command from the processor, relative to the patient.

7. The method of claim 1 including issuing, with the processor, a command to the illumination source, the command causing the illumination source to aim the visible light at the target locations thereby effecting the highlighting of the target locations.

8. The method of claim 1, wherein the image of the person comprises a first image and the additional image comprises a second image, the method further including:
    causing, with the processor, an imaging device to capture the second image, wherein determining the target locations comprises
    registering, with the processor, the second image with the first image.

9. The method of claim 8 wherein the second image comprises an X-ray image or an MRI image.

10. The method of claim 1, further comprising:
    determining, with the processor, a temporal sequence for illuminating the first through nth locations; and
    causing, with the processor, the illumination source to highlight the first through nth locations, with visible light, according to the temporal sequence, and after the first through nth locations have been determined.

11. The method of claim 1, wherein:
    the first through nth locations are determined, respectively, as functions of a location of at least one additional marker, and
    the at least one additional marker is determined, with the processor, based on the image of the person.

12. A method for guiding electrocardiogram (ECG) electrode placement on a person, comprising:
    acquiring an image of the person;
    identifying at least one externally discernable anatomical landmark illustrated in the image of the person;
    acquiring an additional image illustrating an internal anatomical structure of the person;
    identifying at least one internal feature of the person based on the additional image;
    determining, based on a first location of the at least one landmark and a second location of the at least one internal feature, target locations on the person at which first through nth ECG electrodes should be placed; and
    highlighting the target locations on the person with visible light.

13. The method of claim 12, wherein the image of the person comprises a first image, and the additional image comprises a second image, the method further including:
    acquiring the second image with an X-ray imaging device or an MRI imaging device, wherein determining the target locations comprises
    registering, with a processor, the second image with the first image.

14. The method of claim 13 wherein the second image comprises an X-ray image or an MRI image.

15. The method of claim 12, further comprising:
    determining a temporal sequence for highlighting the target locations; and
    highlighting the first through nth locations, with visible light, according to the temporal sequence, and after the first through nth locations have been determined.

16. The method of claim 12, wherein:
    the first through nth locations are determined, respectively, as functions of a location of at least one additional marker, and
    the at least one additional marker is determined based on the image of the person.

17. One or more non-transitory computer-readable media maintaining instructions that, when executed by one or more processors, program the one or more processors to:
    acquire a digital image of a person;
    identify at least one externally discernable anatomical landmark illustrated in the digital image of the person;
    acquire an additional image illustrating an internal anatomical structure of the person;
    identify at least one internal feature of the person based on the additional image;
    determine, based on a first location of the at least one landmark and a second location of the at least one internal feature, target locations on the person at which first through nth ECG electrodes should be placed; and
    cause an illumination source to direct visible light to the target locations.

18. The one or more non-transitory computer-readable media of claim 17, wherein:
    the digital image comprises a first image,
    the additional image comprises a second image,
    the instructions further program the one or more processors to:

cause an imaging device to acquire the second image, wherein determining the target locations comprises registering the second image with the first image.

19. The one or more non-transitory computer-readable media of claim 17, wherein the instructions further program the one or more processors to:
   determine a temporal sequence for highlighting the target locations; and
   cause the first through nth locations to be highlighted, with visible light, according to the temporal sequence, and after the first through nth locations have been determined.

20. The one or more non-transitory computer-readable media of claim 17, wherein:
   the first through nth locations are determined, respectively, as functions of a location of at least one additional marker, and
   the location of the at least one additional marker is determined based on the image of the person.

* * * * *